(12) United States Patent
Ikeda et al.

(10) Patent No.: US 8,092,745 B2
(45) Date of Patent: Jan. 10, 2012

(54) MAGNETIC SENSOR, PRODUCTION METHOD OF THE SAME, AND TARGET SUBSTANCE DETECTING APPARATUS AND BIOSENSOR KIT USING THE SAME

(75) Inventors: Takashi Ikeda, Yokohama (JP); Kazuhisa Okano, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/014,667

(22) Filed: Jan. 26, 2011

(65) Prior Publication Data

US 2011/0117676 A1    May 19, 2011

Related U.S. Application Data

(62) Division of application No. 11/730,778, filed on Apr. 4, 2007, now abandoned.

(30) Foreign Application Priority Data

Apr. 11, 2006   (JP) .................................. 2006-108498

(51) Int. Cl.
    *G01N 33/543*  (2006.01)
(52) U.S. Cl. ............... 422/68.1; 422/82.01; 422/186.01; 436/526; 436/149; 436/806
(58) Field of Classification Search ............... 422/61, 422/186.01, 68.1, 83; 436/526, 149, 806
    See application file for complete search history.

(56) References Cited

U.S. PATENT DOCUMENTS

| 7,387,901 | B2 | 6/2008 | Nishiuma et al. |
| 7,425,455 | B2 | 9/2008 | Fukumoto et al. |
| 2004/0146863 | A1 | 7/2004 | Pisharody et al. |
| 2004/0248282 | A1 | 12/2004 | Sobha et al. |
| 2005/0130296 | A1 | 6/2005 | Pisharody et al. |
| 2005/0244873 | A1 | 11/2005 | Ikeda et al. |
| 2007/0231926 | A1 | 10/2007 | Ikeda |
| 2007/0298510 | A1 | 12/2007 | Imamura et al. |

FOREIGN PATENT DOCUMENTS

| JP | 2005-315678 A | 11/2005 |
| WO | 03/067258 A1 | 8/2003 |

OTHER PUBLICATIONS

Baselt, et al., "A biosensor based on magnetoresistance technology", Biosensors & Bioelectronics, vol. 13, 1998, pp. 731-739.
Graham, et al., "High sensitivity detection of molecular recognition using magnetically labelled biomolecules and magnetoresistive sensors", Biosensors & Bioelectronics, vol. 18, 2003, pp. 483-488.

*Primary Examiner* — Brian R Gordon
*Assistant Examiner* — Shogo Sasaki
(74) *Attorney, Agent, or Firm* — Fitzpatrick, Cella, Harper & Scinto

(57) ABSTRACT

The present invention provides a magnetic sensor which detects a target substance indirectly by making a labeling substance larger than the target substance bond with the target substance contained in a sample in a detection area, and detecting the labeling substance, comprising a capture area which is relatively easy to capture the target substance, and a non-capture area which is relatively hard to capture the target substance, on a surface of a member which is comprised in a detection area, wherein the capture area is surrounded by the non-capture area. Thereby, the sensor enables to detect comparatively accurately the number and concentration of substances which cannot be directly detected, and enables to be used for detection of various target substances.

4 Claims, 6 Drawing Sheets

MAGNETIC SENSOR, PRODUCTION METHOD OF THE SAME, AND TARGET SUBSTANCE DETECTING APPARATUS AND BIOSENSOR KIT USING THE SAME

This application is a divisional of application Ser. No. 11/730,778, filed Apr. 4, 2007, the contents of which are incorporated herein by reference.

BACKGROUND OF THE INVENTION

1. Field of the Invention

The present invention relates to a magnetic sensor for target substance detection and its production method, and an apparatus and a kit for target substance detection using this sensor.

2. Description of the Related Art

As a quantitative immunoassay, a radiometric immunity analysis (RIA: radio immunoassay or IRMA: immunoradiometric assay) has been known for many years. This method labels a competitive antigen or an antibody by a radionuclide, and quantitatively measures the antigen from a measurement result of specific radioactivity. Thus, this method labels a target substance, such as an antigen, and measures this indirectly. Although this method has achieved large contribution in clinical diagnosis since sensitivity is high, there is a problem of safety of a radionuclide, and there is a defect that a facility and an apparatus for exclusive use are necessary. Then, methods of using labels, such as a fluorescent material, an enzyme, an electrochemical luminescence molecule, and a magnetic particle, have been proposed as methods of being easier to handle, for example. An enzyme immunoassay (EIA) which uses an enzyme as a label is a method of making an antigen-antibody reaction performed, making an enzyme-labeled antibody react, adding a substrate to the enzyme and making it color, and performing colorimetry with its absorbance.

Recently, a method of detecting easily a trace amount of magnetic particles used as a labeling substance is proposed by using a magnetoresistance effect film (refer to David R. Baselt et al., Biosensors & Bioelectronics 13, 731 (1998)) (hereafter, "Document 1") and D. L. Graham et al., Biosensors & Bioelectronics 18, 483 (2003) (hereafter, "Document 2").

In Document 1, two or more pieces of magnetic particles with 2.8 µm of diameter are detected using giant magnetoresistance effect (GMR) films in size of 80 µm×5 µm and 20 µm×5 µm. The magnetic film used in the GMR film is an inplane magnetization film, and a magnetic field applied to magnetic particles is applied in a direction perpendicular to a film surface of the magnetic film. Hence, as illustrated in FIG. 4, a stray magnetic field generated by the magnetic particles magnetized by an application of a magnetic field is applied to the magnetic film of the GMR film in an approximately in-plane direction, and magnetization of the magnetic film is aligned in this magnetic field direction. FIG. 4 illustrates a magnetic sensor 200, a magnetic particle 400, a magnetization vector 410, an applied magnetic field vector 420, and a stray magnetic field 430. Magnitude of electric resistance of a magnetoresistance effect film depends on a relative magnetizing direction of two magnetic films. That is, a parallel magnetizing direction makes electric resistance comparatively small and an anti-parallel magnetizing direction makes electric resistance comparatively large. In order to achieve magnetized states of the parallel and anti-parallel, the magnetoresistance effect film includes magnetic materials having such coercive forces that a magnetizing direction of a magnetic film in two magnetic films of the magnetoresistance effect film is fixed and a magnetizing direction of another film is magnetization reversible by a stray magnetic field from a magnetic particle. When a magnetic particle does not exist on a GMR sensor, since a magnetic field in an in-plane direction is not applied to a magnetic film even if an external magnetic field is applied, magnetization reversal does not occur. A detection circuit has construction that a bridge circuit includes fixed resistors, and two sensors, that is, a GMR sensor in which a magnetic particle is not immobilized, and a GMR sensor in which a magnetic particle can be immobilized, and a lock-in amplifier detects potential difference induced in this bridge circuit. In Document 2, a magnetic particle in 2 of diameter is detected using a GMR sensor in the size of 2 µm×6 µm. Similarly to Document 1, the GMR sensor is formed by arranging one in which a magnetic particle can be immobilized, and another in which a magnetic particle is not immobilized, and detects the magnetic particle by comparing output signals of these two GMR sensors. Nevertheless, a magnetic film is an inplane magnetization film, and a magnetic field applied to the magnetic particle is in an in-plane longitudinal direction to the magnetic film.

As described above, detection methods of a magnetic particle using a magnetoresistance effect film perform detection by magnetizing the magnetic particle in a desired direction, and changing a magnetizing direction of the magnetoresistance effect film by a stray magnetic field emitted from the magnetic particle. These methods have advantages that an apparatus, a reagent, and the like which are used for measurement are simply handled, and that it is detectable in a comparatively short time.

For example, when a target substance which is going to be detected is an antigen, immobilization of the magnetic particle on the sensor is performed using an antigen-antibody reaction. That is, a primary antibody is formed on the sensor, a specimen, such as blood which may contain an antigen, is made to react with the antibody, and then, the magnetic particle modified by a secondary antibody is made to react. Because of this series of operations, when the antigen exists in the specimen, bonding of primary antibody-antigen-secondary antibody-magnetic particle occurs on the sensor. If the antigen does not exist, the above-mentioned bonding cannot be performed and the magnetic particle is not immobilized on the sensor as a result.

Since one magnetic particle is immobilized on the sensor to one target substance when the above-mentioned immobilizing method is used, the one target substance is detectable by using the magnetic sensor with high sensitivity.

As labeling substances, various things, such as fluorescent substances, enzymes, electrochemical luminescent substances, radioactive substances, and magnetic substances, exist, and the number and concentration of target substances are detected using a detection unit suitable for a labeling substance.

When a fluorescence label, an enzyme label, an electrochemical luminescence label, or the like is used as a label in an optical measuring method, and detection of a target substance is performed by measuring an optical absorbance, a transmittance, or an amount of light emission. In addition, when using the radioactive label containing a radioactive isotope, specific radioactivity is measured and a quantitation of a target substance is performed. Using the above optical measurement methods and radiation measurement methods has a demerit that a large measuring apparatus is necessary. On the other hand, when a magnetic label proposed recently is used, detection using a small measuring apparatus is possible. In the case of using the magnetic label, a small magnetic sensor detects a magnetic field generated from a magnetic particle. As the magnetic sensor, a hall device or a magnetoresistive element is usable.

In the sensor in Document 2, a film with single composition is formed on the sensor, and substances with which target substances bond, for example, antibodies are arranged uniformly. Although size of a modified magnetic particle used for a biosensor is hundreds of nm to tens of μm, size of substances bonding with target substances, such as antigens, is several nm in many cases. Hence, as shown in FIG. 5A, if antibodies and the like are densely formed on the sensor, even if all the antibodies are absorbed in antigens, since a magnetic particle is far larger than an antibody, there arises a case that magnetic particles may not be immobilized to all the antigens. In consequence, there is a problem that, since the number of the immobilized magnetic particles is remarkably different from the number of the adsorbing antigens, there is a possibility that it becomes hard to detect the number or concentration of the antigens. For example, as illustrated in FIG. 5B, even when antigens are immobilized, the number of magnetic particles is not different from the case illustrated in FIG. 5A although the number of the antigens is different, and the number of magnetic particles and the number of antigens are not in one-to-one correspondence, and hence, the correct number of antigens is not detected.

SUMMARY OF THE INVENTION

The present invention aims at providing a sensor which can solve the problem of detection sensitivity based on relationship between the above-mentioned target substance and label.

A magnetic sensor provided by the present invention is a magnetic sensor which detects a target substance indirectly by making a labeling substance larger than the target substance bond with the target substance contained in a sample in a detection area, and detecting the labeling substance, and is characterized by having a capture area which is relatively easy to capture the above-mentioned target substance, and a non-capture area which is hard to capture the above-mentioned target substance, on a surface of a member which constructs the above-mentioned detection area, and the above-mentioned capture area is surrounded by the above-mentioned non-capture area.

A first aspect of a production method of a magnetic sensor provided by the present invention is a production method of a magnetic sensor which has a capture area which is relatively easy to capture a target substance, and a non-capture area which surrounds the capture area and which is hard to capture the above-mentioned target substance, on a surface of a member which constructs a detection area, and detects the above-mentioned target substance indirectly by making a labeling substance larger than the target substance bond with the target substance contained in a sample in the detection area, and detecting the labeling substance. The present method is characterized by including forming an aluminum film on a film which is made of a material which constructs the above-mentioned non-capture area, anodizing the above-mentioned aluminum film to form a hole, filling up the above-mentioned hole with a material which constructs the above-mentioned capture area, and removing the above-mentioned aluminum film with leaving the above-mentioned filled area and exposing the film which is made of the material which constructs the above-mentioned non-capture area.

Another aspect of the production method of a magnetic sensor provided by the present invention is a production method of a magnetic sensor which has a capture area which is relatively easy to capture a target substance, and a non-capture area which surrounds the capture area and which is hard to capture the above-mentioned target substance, on a surface of a member which constructs a detection area, and detects the above-mentioned target substance indirectly by making a labeling substance larger than the target substance bond with the target substance contained in a sample in the detection area, and detecting the labeling substance. The present method is characterized by including approaching a needle, which includes the material which constructs the above-mentioned capture area, to the film which is made of the material which constructs the above-mentioned non-capture area, applying a voltage between the needle and the films which is made of the material which constructs the above-mentioned non-capture area, and forming a dot, which is made of the material which constructs the above-mentioned capture area, on the film which is made of the material which constructs the above-mentioned non-capture area.

Further aspect is a production method of a magnetic sensor which has a capture area which is relatively easy to capture a target substance, and a non-capture area which surrounds the capture area and which is hard to capture the above-mentioned target substance, on a surface of a member which constructs a detection area, and detects the above-mentioned target substance indirectly by making a labeling substance larger than the target substance bond with the target substance contained in a sample in the detection area, and detecting the labeling substance. The present method is characterized by including forming a hole in a resist film arranged on a film which is made of a material which constructs the above-mentioned non-capture area, forming a material, which constructs the above-mentioned capture area, on the above-mentioned resist film and filling up the above-mentioned hole with a material which constructs the above-mentioned capture area, and removing the above-mentioned resist film, and exposing the film which is made of a material which constructs the above-mentioned non-capture area.

Still another aspect is a production method of a magnetic sensor which has a capture area which is relatively easy to capture a target substance, and a non-capture area which surrounds the capture area and which is hard to capture the above-mentioned target substance, on a surface of a member which constructs a detection area, and detects the above-mentioned target substance indirectly by making a labeling substance larger than the target substance bond with the target substance contained in a sample in the detection area, and detecting the labeling substance. The present method is characterized by including forming a film which is made of the material which constructs the above-mentioned non-capture area, forming a hollow in a surface of the above-mentioned film, and forming the material which constructs the above-mentioned capture area in the hollow.

A detecting apparatus provided by the present invention is a detecting apparatus of a target substance including a magnetic sensor for target substance detection, and a detection unit of detecting capture of a target substance to the above-mentioned sensor based on a signal obtained in the magnetic sensor, and is characterized in that the above-mentioned magnetic sensor is a sensor having the above-mentioned construction, and that the above-mentioned detection unit has a unit of detecting capture of the above-mentioned target substance with comparing a signal, obtained in the above-mentioned sensor, with a reference value.

A kit for target substance detection provided by the present invention is characterized by including a sensor, having the above-mentioned construction, and the above-mentioned labeling substance.

Further features of the present invention will become apparent from the following description of exemplary embodiments (with reference to the attached drawings).

DESCRIPTION OF THE EMBODIMENTS

In view of the problem cited previously, the present invention proposes a magnetic sensor which has structure which lessens difference between the number of labeling substances, and the number of target substances, and which is also suitable for enabling more accurate quantitative detection.

Specifically, the magnetic sensor according to the present invention has a capture area which is relatively easy to capture a target substance, and a non-capture area which is hard to capture the target substance, on a surface of a member which constructs a detection area, and the non-capture area surrounds the capture area. The capture area which is relatively easy to capture a target substance is formed as a submicroscopic area in which the target substance labeled with a labeling substance is easy to immobilize. This area may have a target substance capture function in itself, or may be an area which can immobilize a substance which has a target substance capture function, such as an antibody.

Figure 5A:
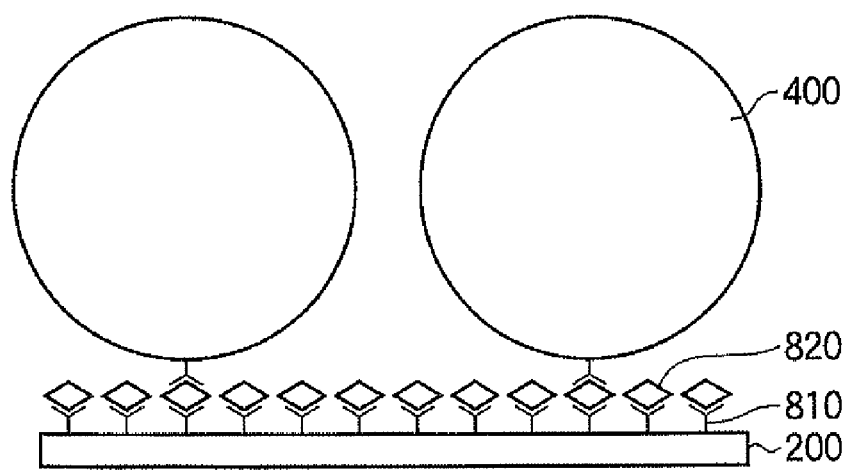
FIGS. 5A and 5B are schematic diagrams illustrating a structural example of a magnetic sensor.
Figure 5B:
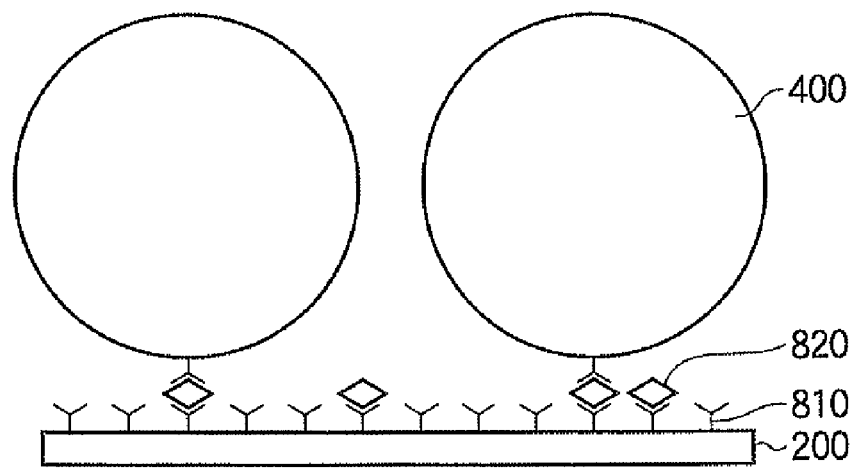

The magnetic sensor according to the present invention solves the problem that the number of labeling substances to the target substances is not in one-to-one correspondence, which is mentioned above using FIGS. 5A and 5B, and can measure an amount of target substances accurately with performing one-to-one correspondence of the number of labeling substances to target substances.

The magnetic sensor according to the present invention prevents a target substance from being captured by a non-capture area since the non-capture area which is relatively hard to capture the target substance surrounds an area which is relatively easy to capture a target substance. This enables accurate correspondence between the target substances captured by the capture area and the labeling substances bonded with these, and enables the detection of the number and concentration of biomolecules, such as antigens and DNA, more accurately.

In the present invention, such construction that a non-capture area is dotted with a plurality of capture areas can be also performed.

In addition, size of one capture area is sufficient for capturing one target substance, and insufficient for capturing a plurality of target substances.

In addition, a plurality of capture areas can be spaced apart by a distance larger than a diameter of a labeling substance.

In the present invention, a capture area can be an area containing gold, and a non-capture area can be an area containing silicon. Then, the area containing silicon can include silicon nitride, silicon oxide, or a mixture of them.

Construction of the sensor according to the present invention enables to have structure suitable for obtaining such construction that a space which a target substance occupies is smaller than a space which a labeling substance occupies, and a plurality of target substance capture areas is spaced apart by a distance larger than the size of a space which a labeling substance occupies. Arrangement of the plurality of target substance capture areas in this way enables to detect the number and concentration of target substances in a sample more accurately.

A magnetic particle and the like can be used as a labeling substance.

As a detection unit combined with the sensor, it is sufficient to select and use a suitable way in each of a case of detecting a target substance directly, and a case of detecting a target substance indirectly using a label.

When capture of a target substance into a target substance capture area is detected as a magnetic change, the sensor according to the present invention can be constructed as a magnetic sensor which can convert a magnetic change into a signal and can output the signal.

The following respective methods can be suitably used for production of a member which constructs the detection area of the magnetic sensor with the above-mentioned construction.

A first method has the following steps.

(1) A step of forming an aluminum film on a film which is made of a material which constructs a non-capture area.

(2) A step of anodizing the aluminum film to form a hole.

(3) A step of filling up the above-mentioned hole with a material which constructs the above-mentioned capture area.

(4) A step of removing the above-mentioned aluminum film with leaving the above-mentioned filled area, and exposing the film which is made of the material which constructs the above-mentioned non-capture area.

In this method, the size of and the gap between respective target substance capture areas can be adjusted by setting conditions of anodic oxidation suitably.

A second method has the following steps.

A step of approaching a needle, which includes a material which constructs the above-mentioned capture area, to a film which is made of a material which constructs a non-capture area, applying a voltage between the needle and the films which is made of the material which constructs the above-mentioned non-capture area, and forming a dot, which is made of a material which constructs the above-mentioned capture area, on the film which is made of the material which constructs the above-mentioned non-capture area.

In this method, a form and size of a dot, and the gap between respective dots can be adjusted according to a gap between the needle and the capture area, the material type which constructs the capture area, application conditions of the voltage, positions of the needle and the film, which includes the material which constructs the non-capture area, at the time of a voltage application, and the like.

A third method has the following steps.

(1) A step of forming a hole in a resist film arranged on a film which is made of a material which constructs a non-capture area.

(2) A step of forming a material, which constructs the above-mentioned capture area, on the above-mentioned resist film, and filling up the above-mentioned hole with a material which constructs the above-mentioned capture area.

(3) A step of removing the above-mentioned resist film, and exposing the film which is made of the material which constructs the above-capture area.

In this method, positions of (gaps between) the target substance capture areas are determined by the holes provided in the resist film.

A fourth method has the following steps.

(1) A step of forming a film which is made of a material which constructs a non-capture area.

(2) A step of forming a hollow in a surface of the above-mentioned film.

(3) A step of forming a material which constructs the above-mentioned capture area in the above-mentioned hollow.

For formation of the material, which constructs the capture area, in the hollows in this method, a cluster beam method or the like can be used suitably.

A material for forming the capture area which is relatively easy to capture a target substance includes gold.

A material for forming the non-capture area which is relatively hard to capture a target substance includes a material containing silicon, and more specifically, silicon nitride and silicon oxide.

A target substance detecting apparatus can be constructed using at least the sensor with the above-mentioned construction, and a detection unit of detecting capture of a target substance to the sensor based on a signal obtained from the sensor.

Furthermore, a kit for target substance detection can be provided using at least the sensor with the above-mentioned construction, and a labeling substance. Moreover, a kit for target substance detection can be provided using at least the detecting apparatus with the above-mentioned construction, and a labeling substance. Various kinds of reagents for preparing a sample and making a sample react with the sensor can be further included in this kit.

Hereafter, the present invention is described in detail below with making detection of an antigen in a sample solution, in which a labeling substance is a magnetic particle, as an example.

Figure 1:
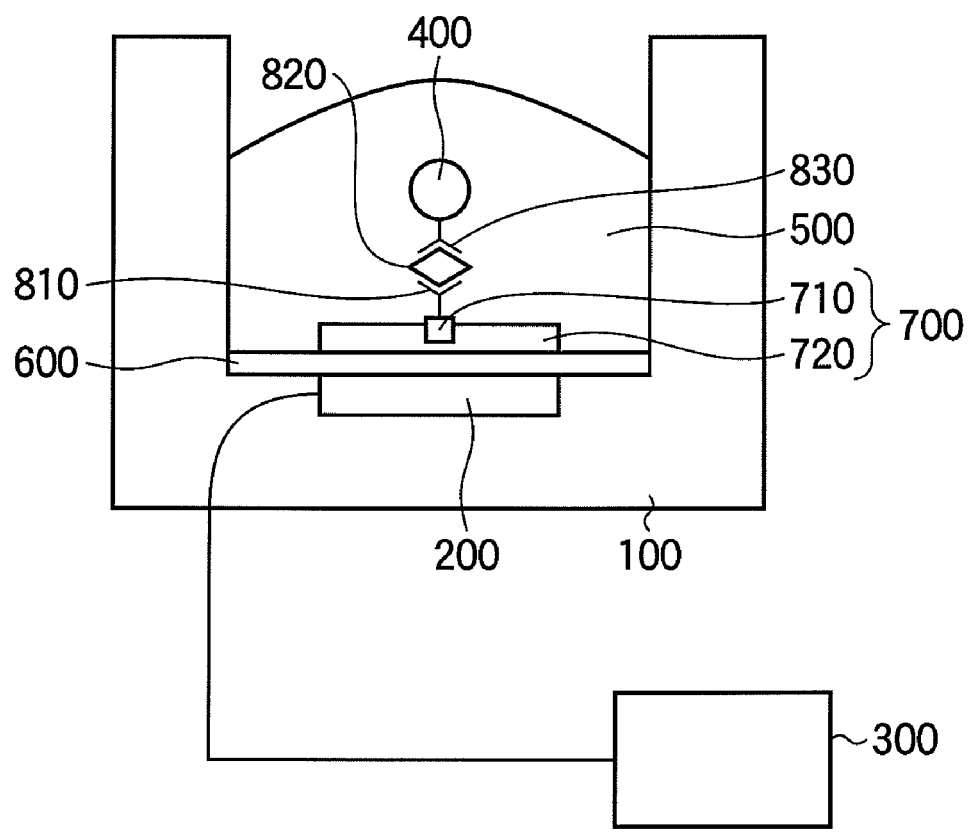
FIG. 1 is a conceptual diagram for describing a structural example of a sensor of the present invention.

As illustrated in FIG. 1, a magnetic sensor 200 is formed in a housing 100, and a magnetic sensor 200 is connected to an external detection circuit 300. The magnetic sensor 200 may be any magnetic field detecting element, such as a magnetoresistive element or a hall device. Among them, for detecting a weak stray magnetic field from the magnetic particle 400, what has good sensitivity is suitable. As such an element, a TMR (Tunneling Magnetoresistance) element which is a magnetoresistive element, or a BMR (Ballistic Magnetoresistance) element is used suitably. In order to insulate a sample 500 and the magnetic sensor 200 electrically, an insulating film 600 is formed on the magnetic sensor 200. Nevertheless, when there is no necessity of insulating the sample 500 from the magnetic sensor 200, the insulating film 600 may not be formed. An immobilization film 700 formed so that an area 710 which is comparatively easy to immobilize (relatively easy to capture) an antigen 820 which is a target substance, and an area 720 which is comparatively hard to immobilize (relatively hard to capture) the antigen 820 may be intermingled is formed on the insulating film 600. Here, members 710, 720, and 700 construct a member which constructs a detection area. The area 710 which is comparatively easy to immobilize a target substance is formed by immobilizing to a predetermined area a primary antibody 810 which adsorbs specifically to a substance to be detected, that is, the antigen 820 which is a target substance. A state of one primary antibody 810 being immobilized in one area is satisfactory, and it is controllable by an area of the area 710, concentration of an antibody, an immobilizing process, and the like. Subsequently, the sample 500 is contacted to the primary antibody 810. When the antigen 820 which is a target substance exists in the sample 500, the antigen 820 bonds with the primary antibody 810. Furthermore, when injecting the magnetic particle 400 in which the secondary antibody (antibody bonded in a position which a primary antibody of an antigen has not bonded) 830 specifically bonded with the antigen 820 is modified, the magnetic particle 400 is immobilized in a magnetic detection area through the primary antibody 810, antigen 820, and secondary antibody 830.

According to the above-mentioned method, since the magnetic particle 400 is immobilized to the antigen 820 immobilized to the primary antibody 810 at a high rate through the secondary antibody 830, the number and concentration of the antigens 820 can be detected accurately.

Figure 6:
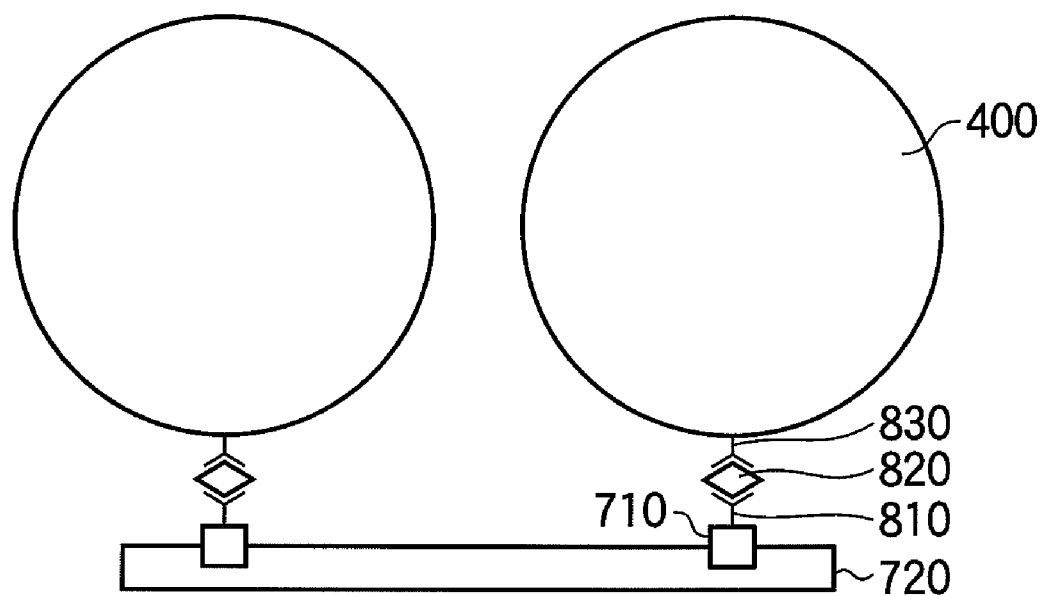
FIG. 6 is a conceptual diagram for describing a structural example of a sensor of the present invention.

Here, a more suitable embodiment of the present invention will be described using FIG. 6. FIG. 6 illustrates an example that two areas 710 which are relatively easy to capture the antigens 820, which are target substances, in the sensor construction illustrated in FIG. 1 are arranged. Thus, this figure is made by illustrating two areas 710 which are easy to capture an antigen, and extracting the area 720, which is relatively hard to capture the antigen 820, the primary antibody 810, the secondary antibody 830, and the magnetic particle 400 from FIG. 1. Other construction is the same as that illustrated in FIG. 1. In the example illustrated in FIG. 6, each of the two areas 710 which are easy to capture an antigen has size that one target substance is captured, but has size that a plurality of capture substances cannot be captured. Furthermore, the two areas 710 which are easy to capture an antigen are spaced apart by a distance larger than a diameter of the magnetic particle 400. Thereby, since the antigen 820 and the magnetic particle 400 which is a labeling substance become in one-to-one correspondence, there arises no such drawback that the number of antigens (concentration) cannot be grasped accurately, which is described with referring to FIG. 5B. Thereby, the number (concentration) of target substances can be measured more accurately.

As the antibody used for the present invention, what are conventionally used are usable. In addition, similarly, various kinds of things can be used as the secondary antibody made to be immobilized to a magnetic particle. As the sample, what antibodies of such as target substances (protein, nucleic acid, and sugar chain), allergens, bacterias, and viruses can recognize specifically become objects. In addition, the present invention can detect any substance so long as it is a substance which can immobilize directly or indirectly a magnetic particle, without limiting to detection of a biomolecules.

A kit for target substance detection can be provided using at least the sensor according to the above-mentioned construction, and a labeling substance.

EXAMPLES

Hereafter, the present invention will be described in detail with citing examples.

Example 1

In this example, an example of a production method of a magnetic sensor according to the present invention will be described with FIGS. 2A to 2I.

Figure 2A:
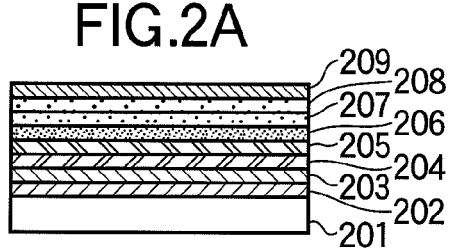
FIGS. 2A, 2B, 2C, 2D, 2E, 2F, 2G, 2H and 2I are conceptual diagrams describing an example of production processes of the sensor of the present invention.

On a surface of a silicon wafer 201, a multilayer structure is obtained by sequentially stacking a Cr film 202 at 20 nm film thickness, a Pt film 203 at 20 nm film thickness, an MnIr film 204 at 10 nm film thickness, an FeCo film 205 at 5 nm film thickness, an $Al_2O_3$ film 206 at 1.6 nm film thickness, an FeCo film 207 at 5 nm film thickness, an NiFe film 208 at 20 nm film thickness, and a Pt film 209 at 5 nm film thickness by magnetron sputtering (FIG. 2A). As for the $Al_2O_3$ film 206, oxygen deficiency is compensated by forming a film using an $Al_2O_3$ target, introducing an $O_2$ gas in a film formation chamber, and performing plasma oxidation. Starting from a silicon wafer 201 side, the Cr/Pt multilayer film becomes a base electrode of a TMR element, the MnIr/FeCo multilayer film becomes a pin layer (layer whose magnetizing direction is fixed) of a TMR film, the $Al_2O_3$ film 206 becomes a tunnel film of the TMR film, the FeCo/NiFe multilayer film becomes a free layer (layer whose magnetizing direction changes with an applied magnetic field easily) of the TMR film, and the Pt film 203 becomes a protective layer for preventing deterioration of the magnetic film at the time of processing.

Figure 2B:
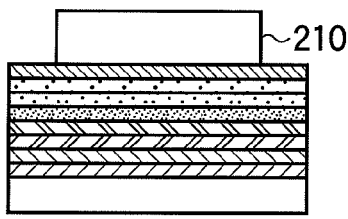

After coating a resist film at about 1 μm uniform film thickness by a spin coater on a surface of the multilayer film and baking the multilayer structure, patterning is performed into a desired form with ultraviolet rays. Then, by performing the baking again, immersing the multilayer structure in a developing solution, and cleaning the multilayer structure with deionized water, a resist film 210 with a desired pattern shape is obtained. Let the resist pattern form be a circular form of 30 μm diameter in this example (FIG. 2B). Publicly-known materials can be used as the material for resist patterning, such as developing solutions for the resist film, and patterning processing.

Figure 2C:
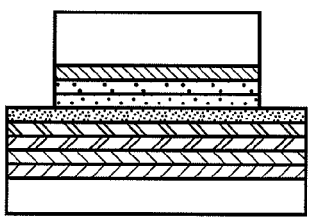
Figure 2D:
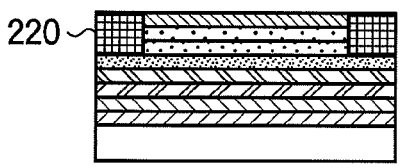

Subsequently, etching from a surface of the multilayer film to a surface of the $Al_2O_3$ film 206 is performed by dry etching using an Ar gas (FIG. 2C). Furthermore, an inter-layer insulating film 220 which includes $Al_7O_3$ is formed by introducing a mixed gas of Ar and $O_2$, and performing magnetron sputtering using an $Al_2O_3$ target (FIG. 2D). Then, the resist film and the $Al_2O_3$ film formed on the resist film are removed by cleaning the multi-layer structure ultrasonically with immersing the multi-layer structure into a resist remover.

Figure 2E:
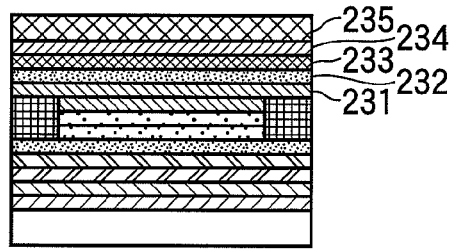

On a surface of the multi-layer structure in which the fine patterning was performed, further, a Pt film 231 at 30 nm film thickness, an $Al_2O_3$ film 232 at 10 nm film thickness, an SiN film 233 at 30 nm film thickness, a Cr film 234 at 5 nm film thickness, and an Al film 235 at 5-μm film thickness are sequentially formed (FIG. 2E). The Pt film 231 in this film formation is a top electrode of the TMR element, and the $Al_2O_3$ film 232 is an insulating film between the TMR element and the multilayer film on the element. A distance between a target substance and a magnetic sensor is important in sensitivity, and the shorter the distance is, the higher the magnetic sensor is expected to be in sensitivity. Hence, the thinner the multilayer film formed on the free layer of the TMR film is in a range where each film plays its function, the better the multilayer film is, and hence, each film thickness is not limited to the value illustrated in this example.

Figure 2F:
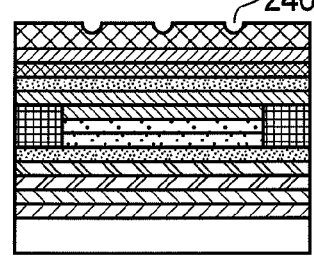

Then, a needle tip with a small radius of curvature at an end is pressed against the Al film surface, and hollows 240 are formed (FIG. 2F). In this example, the needle whose radius of curvature is about 10 nm is used. In addition, let a gap between adjacent needle tips be 500 nm.

Figure 2G:
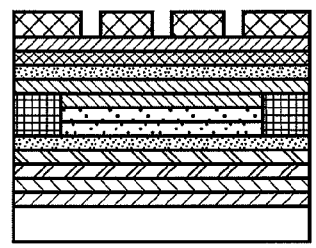

The multi-layer structure on a surface of which the hollows 240 are formed is immersed into an oxalic acid solution, and the Al film is anodized. At this time, anodic oxidation advances with making the portions, in which the hollows are formed in the Al film, as starting points. The anodic oxidation is stopped when holes formed reach the Cr film. An average diameter of the holes formed by the anodic oxidation is about 15 nm (FIG. 2G).

Figure 2H:
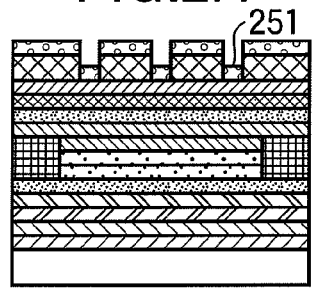

After cleaning a surface of a multilayer film structure side which has the holes which are given anodizing, Au dots 251 are formed on bottoms of the holes formed in the Al film (FIG. 2H). Since aspect ratios of these holes are remarkable high, it is suitable that Au atoms come flying at a vertically high rate to the surface of the multilayer film structure. Hence, low pressure remote sputtering, SIS (Self Ionized Sputtering), collimate sputtering, ionized sputtering, and the like are generally known as such film formation methods.

Figure 2I:
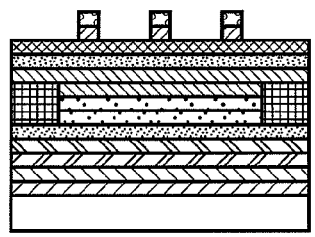

After film formation of Au is completed, wet etching of the Al film is performed with an alkali solution. When the Au film formed on the Al film becomes an overcoat at this time and etching does not advance, etching should be performed after removing the Au film on the surface of the Al film by polishing. After removing the Al film, dry etching of the Cr film is performed using a chlorinated gas (FIG. 2I). Nevertheless, since it is necessary to leave the Cr films which exist under the Au dots, it is suitable to make chlorine ions collide with Cr surfaces at high speed, and to make bottoms of the Au dots not etched as much as possible.

Owing to the above-mentioned process, the magnetic sensor of the present invention in which the minute Au dots which dot the SiN film in a 500 nm pitch are formed on the TMR element can be produced.

Although a TMR element is used as a magnetic sensor in this example, various magnetic sensors, such as a GMR element, a BMR element, a Hall element, an abnormal Hall element, and a planer Hall element, are usable.

The number of magnetic particles in liquid can be detected using the magnetic sensor of the present invention.

A detection circuit is connected between the top electrode and base electrode of the magnetic sensor of the present invention, and initial resistance before measurement is measured. When a magnetic particle which is an object for detection is remarkably small, and super paramagnetism is exhibited, detection is performed by applying a magnetic field to the magnetic particle from the external. Hence, also when measuring the initial resistance, similarly, a magnetic field is applied. Magnitude of the applied magnetic field is magnitude which can give a stray magnetic field of magnitude, by which the magnetic particle can be detected, to the magnetic sensor. Although the magnitude is not specified strictly in particular, in this example, the magnetic field is made to be the magnetic field of 500 Oe perpendicular to the magnetic sensor surface. In addition, the detection circuit may be such a highly sensitive detection circuit using a bridge circuit or a lock-in amplifier which is described in Document 1, or may be a circuit with simple construction which includes a current generator and a voltmeter.

Subsequently, the magnetic sensor is immersed into a sample solution including a magnetic particle as a target substance. The magnetic particle which is an object for detection is immobilized on a surface of the magnetic sensor by bonding of the Au dot on the surface of the magnetic sensor, and a thiol group modified by the magnetic particle. Since the magnetic particles which are floating in the sample solution are gradually immobilized while time passes, the number of the magnetic particles can be known by comparing the detection signal of the magnetic sensor at the time when all magnetic particles are immobilized, and the initial value. Alternatively, even before all magnetic particles are immobilized, the number of all magnetic particles can be known by estimating a saturation value of the detection signal from the change of the detection signal to the immobilization time. When many magnetic particles exist in a sample solution and all magnetic particles cannot be immobilized on the magnetic sensor, what is necessary is just to immerse many magnetic sensors into the sample solution.

Furthermore, bio sensing can be performed using the magnetic sensor of the present invention. Example of the sensing will be described further with reference to FIG. 1. In addition, the Au dots 251 in the construction of FIGS. 2A to 2I are equivalent to the area 710 in FIG. 1 which is comparatively easy to immobilize target substances, the surface of the SiN film 233 is equivalent to the area 720 which is comparatively hard to immobilize target substances, and the immobilization film 700 is formed of these.

Furthermore, the magnetic sensor obtained through the steps of FIGS. 2A to 2I is illustrated as reference numeral 200 in FIG. 1.

After hydrophilization treatment is performed first, amino silane coupling agent treatment of the surface of the immobilization film 700 is performed. Furthermore, a primary antibody 180 which captures a desired antigen by making an amino group derived from an amino silane coupling agent, and peptide chains chemically bonded using a cross linking agent, such as glutaraldehyde, for making the primary antibody 810 immobilized is immobilized.

Detection of a prostatic specific antigen (PSA) known as a marker of prostate cancer according to the following protocol can be tried using this detection device. Size of the PSA is as small as about several nm. A primary antibody 810 which recognizes the PSA is immobilized in the detection device.

(1) Dip the detection device in a phosphate buffered saline including PSA which is an antigen 820, and incubate for 5 minutes.

(2) Clean the detection device, which passed through step (1), with phosphate buffered saline, and flush the unreacting PSA.

(3) Dip the detection device, which passed through step (2), in a phosphate buffered saline including an anti-PSA antibody labeled by the magnetic particle 400, and incubate for 5 minutes.

(4) Clean the detection device, which passed through step (3), with phosphate buffered saline, and flush the labeled antibody unreacting.

Nevertheless, an average diameter of the magnetic particles 400 is about 400 nm, and the magnetic particles 400 exhibit super paramagnetism. Since the immobilization films 700 are formed in the interval of about 500 nm, the antigens 820 are not immobilized in an area where the magnetic particles 400 cause steric hindrance.

First, a constant current is flowed through the TMR film in a TMR element 200 which is a magnetic sensor element in a non-magnetic field, and a voltage of the TMR film at this time is measured. Subsequently, a downward external magnetic field of magnitude of 500 Oe is applied to the magnetic particle 400 immobilized through the antigen-antibody reaction on a surface of the TMR film to orient magnetization of the magnetic particle 400 downward. From the magnetic particle 400, a stray magnetic field is generated, a synthetic magnetic field of the external magnetic field and the stray magnetic field is applied to the free layer, and magnetization reversal occurs. In this state, a constant current is flowed again through the TMR film, a variation of the voltage is measured, and the antigens 820 can be detected in the sample solution.

Example 2

Although the production method of the Au dot pattern using anodic oxidation was described in the first example, Au dots can be also formed into a desired pattern using an Au target which has a needle-shaped section.

An SiN film 233 at 30 nm film thickness is formed on a surface of the multilayer film structure in the state that the magnetic sensor of FIG. 2D in the first example is formed. Then, a resist film is coated at about 1-μm uniform film thickness by a spin coater. Subsequently, patterning is performed with ultraviolet rays after baking, for example, so that a resist film may cover an area where Au dots are not formed, such as an area other than an area above the sensor element. Then, the multilayer film structure is baked again, and is immersed in a developing solution to be cleaned with deionized water, and then, a resist film with a desired pattern shape is obtained. Next, an acicular Au target and a treated surface are arranged with making the acicular Au target and the treated surface face and approach each other in parallel. When sputtering of the Au target is performed in this state, Au atoms from Au of a needle tip come flying to an element surface, and an Au dot is formed only directly under the needle tip. Then, the element is ultrasonically cleaned with being immersed in a resist remover. The resist film and the Au dots formed on it are removed, and the sensor for target substance detection which has a magnetic sensor is obtained. When a target substance is indirectly detected using a labeling substance, the acicular target where needles are arranged at the pitch larger than a grain size of the labeling substance is used so that the labeling substances may be immobilized to the target substances immobilized on the magnetic sensor 200.

In addition, publicly known materials and methods can be used for formation and removal of the pattern which includes the resist film.

On the other hand, the acicular Au target may be a target that the entire target is formed from Au, or may also have Au portions, such as a target that an Au film is provided on an acicular base surface.

Example 3

Furthermore, by forming micropores in an upper portion of the element by resist film patterning, and forming Au films on the pores, Au dots can be also formed into a desired pattern.

An SiN film 233 at 30 nm film thickness is formed on a surface of the multilayer film structure in the state that the magnetic sensor of FIG. 2D in the first example is formed. Then, a resist film is coated at about 200 nm uniform film thickness by a spin coater. After baking, holes are formed by radiating electron rays in positions where Au dots are formed. Then, the multilayer film structure is baked again, and is immersed in a developing solution to be cleaned with deionized water, and then, a resist film with a desired pattern shape is obtained. Diameter of the holes formed is about φ50 nm diameter, and the interval between adjacent holes is made larger than the grain size of labeling substances. Subsequently, an Au film is formed in each hole by a low directive film formation apparatus, and an Au dot that a film thickness of a center portion is thick is formed in a bottom of each hole. Then, the element is ultrasonically cleaned with being immersed in a resist remover. The resist film and the Au dots formed on it are removed. In addition, publicly known materials and methods can be used for formation and removal of the pattern which includes the resist film.

Furthermore, an entire surface of the multilayer film structure is dry-etched with an Ar gas, and a diameter of each Au dot is made small to desired size. At this time, in order to prevent liberation of N from the SiN film, a mixed gas of Ar and $N_2$ may be used as the etching gas. The sensor for target substance detection which contains the magnetic sensor is obtained through the above process.

Example 4

Figure 3A:
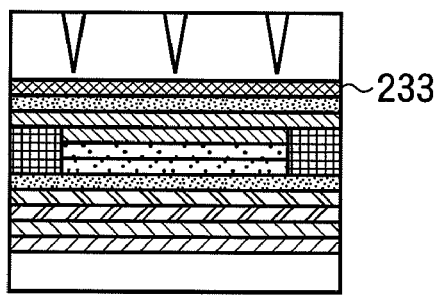
FIGS. 3A and 3B are conceptual diagrams for describing a structural example of the sensor of the present invention.
Figure 3B:
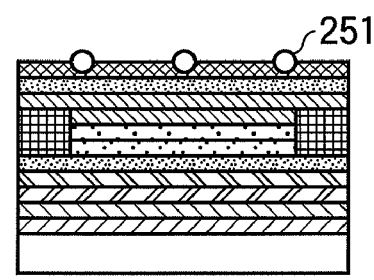
Figure 4:
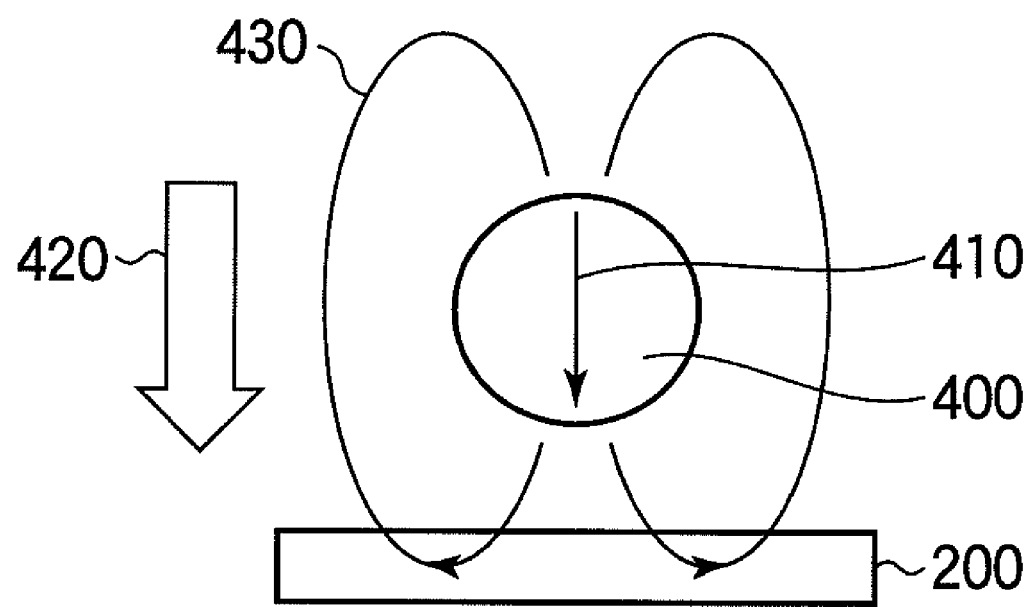
FIG. 4 is a schematic diagram illustrating a structural example of a magnetic sensor.

In the third example, a comparatively low dose amount of electron rays are radiated on the resist film coated on the SiN film 233 at 30 nm film thickness. Then, the multilayer film structure is baked again, and is immersed in a developing solution to be cleaned with deionized water, and then, a resist pattern as illustrated in FIG. 3A is formed. The pitch of hollows in the resist pattern is made larger than the grain size of labeling substances. Then, the resist film is successively made thin by dry etching, and when the lower SiN film 233 is slightly etched, the etching is stopped. After removing the resist film, by flying Au atoms on a surface of the SiN film 233 using a cluster beam, Au atoms gather in the hollows of the SiN film 233, and the Au dots 251 as illustrated in FIG. 3B are formed. The sensor for target substance detection which contains the magnetic sensor is obtained through the above process.

In addition, publicly known materials and methods can be used for formation and removal of the pattern which includes the resist film.

According to the exemplary examples of the present invention, a sensor which can detect comparatively accurately the number and concentration of substances which cannot be directly detected, and which can be used for detection of various target substances can be provided.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2006-108498, filed Apr. 11, 2006, which is hereby incorporated by reference herein in its entirety.

What is claimed is:

1. A method for magnetic sensing using a magnetic sensor to detect a target substance in a sample,
    wherein the magnetic sensor comprises a magnetic field detecting element,
    wherein the method comprises detecting the target substance in the sample indirectly by immobilizing the target substance to a surface of the magnetic field detecting element, by making a labeling substance larger than the target substance bond with the target substance immobilized on the surface of the magnetic field detecting element, and by detecting a change of magnetic field using the magnetic field detecting element, the change of magnetic field being due to the target substance being immobilized to the magnetic field detecting element and consequently the target substance being close to the magnetic filed detecting element,
    wherein the labeling substance is a magnetic particle,
    wherein the surface of the magnetic field detecting element to which the sample is in contact comprises a first plurality of areas each of which has a substance that specifically captures the target substance,
    wherein each of the first plurality of areas is surrounded by a second area which does not have the substance that specifically captures the target substance,
    wherein a distance between respective ones of the first plurality of areas is larger than a diameter of the labeling substance, and
    wherein each of the first plurality of areas has a size such that only one molecule of the target substance is captured.

2. The method according to claim 1, wherein the first plurality of areas is formed as a plurality of dots.

3. The method according to claim 1, wherein each of the first plurality of areas comprises gold, and the second area comprises silicon.

4. The method according to claim 3, wherein the second area comprises either silicon nitride or silicon oxide.

* * * * *